(12) United States Patent
Touitou

(10) Patent No.: US 9,023,374 B2
(45) Date of Patent: May 5, 2015

(54) SANITIZING COMPOSITIONS

(75) Inventor: Elka Touitou, Hod Hasharon (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 13/499,793

(22) PCT Filed: Oct. 1, 2010

(86) PCT No.: PCT/IB2010/002507
§ 371 (c)(1),
(2), (4) Date: Jul. 17, 2012

(87) PCT Pub. No.: WO2011/039630
PCT Pub. Date: Apr. 7, 2011

(65) Prior Publication Data
US 2012/0328548 A1    Dec. 27, 2012

Related U.S. Application Data

(60) Provisional application No. 61/248,229, filed on Oct. 2, 2009.

(51) Int. Cl.
| | |
|---|---|
| *A61K 47/10* | (2006.01) |
| *A61K 31/255* | (2006.01) |
| *A61K 31/355* | (2006.01) |
| *A61K 31/685* | (2006.01) |
| *A61K 31/78* | (2006.01) |
| *A61K 31/045* | (2006.01) |
| *A61K 9/00* | (2006.01) |
| *A01N 31/02* | (2006.01) |
| *A61K 8/34* | (2006.01) |
| *A61K 47/20* | (2006.01) |
| *A01N 41/04* | (2006.01) |
| *A01N 43/90* | (2006.01) |
| *A61K 8/55* | (2006.01) |
| *A61K 47/32* | (2006.01) |
| *A61K 8/67* | (2006.01) |
| *A61K 8/02* | (2006.01) |

(52) U.S. Cl.
CPC ............... *A01N 31/02* (2013.01); *A61K 8/342* (2013.01); *A61K 47/20* (2013.01); *A61K 8/345* (2013.01); *A61K 8/34* (2013.01); *A61K 8/553* (2013.01); *A61K 47/32* (2013.01); *A61K 8/678* (2013.01); *A61K 8/02* (2013.01); *A01N 41/04* (2013.01); *A01N 43/90* (2013.01)

(58) Field of Classification Search
CPC ....... A61Q 17/005; A61Q 19/00; A61K 8/44; A61K 2800/592; A61K 8/37; A61K 31/045; A61K 47/10; A61K 8/34; A61K 47/20; A61K 8/342
See application file for complete search history.

(56) References Cited

U.S. PATENT DOCUMENTS

| | | | | |
|---|---|---|---|---|
| 2,664,382 | A | * | 12/1953 | Omohundro et al. ........... 514/67 |
| 5,891,422 | A | | 4/1999 | Pan et al. |
| 6,190,674 | B1 | | 2/2001 | Beerse et al. |
| 2004/0253189 | A1 | * | 12/2004 | Maxwell et al. ................ 424/49 |
| 2005/0019421 | A1 | * | 1/2005 | Hobbs et al. .................. 424/616 |
| 2005/0186147 | A1 | * | 8/2005 | Tamarkin et al. ............... 424/47 |
| 2008/0253976 | A1 | | 10/2008 | Scott et al. |
| 2009/0068287 | A1 | | 3/2009 | Welsh et al. |
| 2009/0304799 | A1 | * | 12/2009 | Baker et al. ................... 424/489 |

FOREIGN PATENT DOCUMENTS

| | | | |
|---|---|---|---|
| DE | 102006023368 | A1 * | 11/2007 |
| EP | 0629345 | | 12/1994 |
| EP | 0629345 | A1 * | 12/1994 |
| FR | 2972347 | | 9/2012 |
| WO | 0238181 | | 5/2002 |
| WO | WO 2005087195 | A2 * | 9/2005 |

OTHER PUBLICATIONS

Hao et al (Host-Seeking and Blood-Feeding Behavior of *Aedes albopictus* (Diptera: Culicidae) Exposed to Vapors of Geraniol, Citral, Citronellal, Eugenol, or Anisaldehyde, 2008, Journal of Medical Entomology, vol. 45, pp. 533-539).*
Eludril Solution ed, Vidal L, Jan. 1, 1987, Dictionnaire Vidal. 1995; [Dictionnaire Vidal], Paris, Editions Du Vidal, FR, p. 521.
Mintel: Mouth Rinse Solution, GNPD, Feb. 1, 2006, 1 page.
International Search Report for International Application No. PCT/IB 10/02507, completion date Jan. 21, 2011.
Supplementary European Search Report for EP Application No. EP 10 81 9990, completion date Aug. 16, 2013.

* cited by examiner

*Primary Examiner* — Cherie M Stanfield
*Assistant Examiner* — Mark V Stevens
(74) *Attorney, Agent, or Firm* — Browdy and Neimark, PLLC

(57) ABSTRACT

Provided are novel compositions exhibiting highly effective antiviral, antimicrobial and/or antifungal activity. The compositions of the invention can be used for sanitizing and/or disinfecting surfaces, e.g., inanimate and/or animate surfaces. Preferred compositions include a synergistic combination of an alcohol, docusate, geraniol and, optionally, menthol. The invention provides compositions that have high antimicrobial activity, yet are mild, non-irritating, quick drying, non-sticky and not drying to the skin. Processes for manufacturing and using the compositions and products containing such compositions are also disclosed.

26 Claims, 2 Drawing Sheets

Fig. 1 log₁₀ reduction of Vaccinia virus after 30 seconds exposure log₁₀ reduction of Vaccinia virus after 60 seconds exposure

SANITIZING COMPOSITIONS

BACKGROUND OF THE INVENTION

Hand transmission of viruses is recognized as an important factor in the occurrence of respiratory and enteric diseases. Transfer of virus can occur to and from hands, as well as between hands and fomites (a fomite is an object or substance capable of carrying infectious organisms). At high concentrations, alcohol is rapidly bactericidal against gram positive and gram negative vegetative bacteria. The U.S. Food and Drug Administration ("FDA") has determined that alcohol at 60-95% concentrations in aqueous solutions is safe and effective as a germicide and therefore acceptable.

Certain enveloped viruses are susceptible to high concentrations of alcohol as well. However, low concentrations of alcohol are not considered to be effective in inactivating viruses. Moreover, alcohol, even at high concentrations, has poor activity against nonenveloped viruses.

Norovirus, a non enveloped virus, is the most common cause of viral gastroenteritis. Surveillance study determined that around 90% of all non-bacterial outbreaks in Europe could be attributed to norovirus (Lopman et al., 2003). This resilient virus can be spread by person to person contact, via aerosols, through contaminated food and water as well as via environmental surfaces. It is capable of causing sporadic cases as well as large outbreaks which typically occur within institutionalized settings such as hospitals, schools or cruise ships. Feline calicivirus is currently the most widely used surrogate virus as it has a similar genome organization, capsid architecture and biochemical properties as that of norovirus.

Doultree et al., "Inactivation of feline calicivirus, a Norwalk virus surrogate," *J. Hosp. Infec.* 1999, 41:51-57, reported that quaternary ammonium product, detergent and ethanol failed to inactivate the virus.

Duizer et al., "Inactivation of Caliciviruses," *Applied and Environmental Microbiology*, August 2004, p, 4538-4543, reported that inactivation of feline calicivirus, a widely studied norovirus surrogate, by 70% w/w ethanol in room temperature was inefficient with less than $\log_{10} 2$ reduction after 8 minutes and $\log_{10} 3$ reduction after 30 minutes.

Hand sanitizers are the most popular amongst sanitizers. The active ingredient in sanitizers is in most cases ethanol, isopropanol, or n-propanol. A variety of preparations are available, including gels, foams and liquid solutions. Hand sanitizers containing alcohol are more effective at killing germs than soaps. On the other hand, the alcohol-based sanitizers, while having demonstrated good antimicrobial activity, have poor antiviral activity against nonenveloped viruses.

In order to achieve antiviral activity non-GRAS ingredients (i.e., ingredients that are not "Generally Recognized as Safe" by US FDA standards) have been added to sanitizing compositions containing alcohol at high concentrations, e.g., hydrogen peroxide, sulfonates, thiocyanate, formaldehyde, organic acids in high concentration, cationic surfactants, organic amines, cationic polymers or combinations thereof.

FDA (ISSA Guide to the Regulations of Antibacterial Hand Soaps) has determined that alcohol 60-95% in an aqueous solution is safe and effective as a germicide and therefore acceptable. In ethanol based sanitizing compositions on the market, ethanol needs to be at a high concentration (60-95%). These products have many disadvantages, like drying and irritating of the skin, especially on repeated use, by removing the protective layer of the skin. In order to overcome the drawbacks of dryness and irritation, compositions were previously formulated by using humectants, silicones, detackifiers (U.S. Pat. No. 6,423,339 to Procter & Gamble) and/or polymers as excipients in the sanitizing compositions.

However, there remains an unmet need for highly effective sanitizing compositions exhibiting strong antiviral activity, preferably comprising safe GRAS ingredients exhibiting minimal side-effects. The present invention provides such compositions.

SUMMARY OF THE INVENTION

The present invention successfully addresses unmet medical needs, by providing innovative and highly effective sanitizing compositions and methods for using the compositions to disinfect or sanitize surfaces such as, for example, hands, mouth cavity, skin and skin appendages, surfaces, instruments, food and food contact surfaces.

It was surprisingly found that the combination of an alcohol (e.g., a volatile or $C_1$-$C_4$ alcohol such as, e.g., ethanol, isopropanol, or a combination thereof, particularly ethanol), docusate, and geraniol, synergistically provide high antiviral activity. It was also surprisingly found that combinations of alcohol, geraniol, docusate, and, optionally, menthol exhibit strong synergistic antiviral and antimicrobial effects. The compositions of the present invention may further include water, a glycol, a phospholipid, or a combination thereof, as well as other additional ingredients.

The compositions of the present invention can be used effectively to inactivate viruses in the mouth cavity, on skin and skin appendages, hands, surfaces, instruments, food surfaces and food. The compositions of the present invention can be used, for example, as sanitizing and/or disinfecting antiviral microbicidal and antifungal compositions for sanitizing and/or disinfecting hands, skin, mouth cavity, lips, mucosae, surfaces, food contact surfaces, instruments, food and fruit, skin and skin appendages. More particularly, the compositions of the present invention can be used as antiviral compositions for inactivating viruses. The compositions of the present invention also have the advantage of being able to utilize ingredients that are generally regarded as safe (GRAS) by the US FDA and are listed by the FDA Everything Added to Food in the United States (EAFUS) database.

These and other aspects of the invention will become apparent from the description of the invention, which follows below.

BRIEF DESCRIPTION OF THE DRAWINGS

FIG. 1 depicts the synergistic antiviral activity of formulations from Example 1 and Example 2 tested for their antiviral activity against Vaccinia virus after 30 seconds exposure, and for comparison compositions A,B,C and D containing ethanol 25% only, 0.1% sodium docusate in 25% ethanol, 0.1% geraniol in 25% ethanol and 0.2% menthol in 25% respectively.

DETAILED DESCRIPTION OF THE INVENTION

Figure 2:
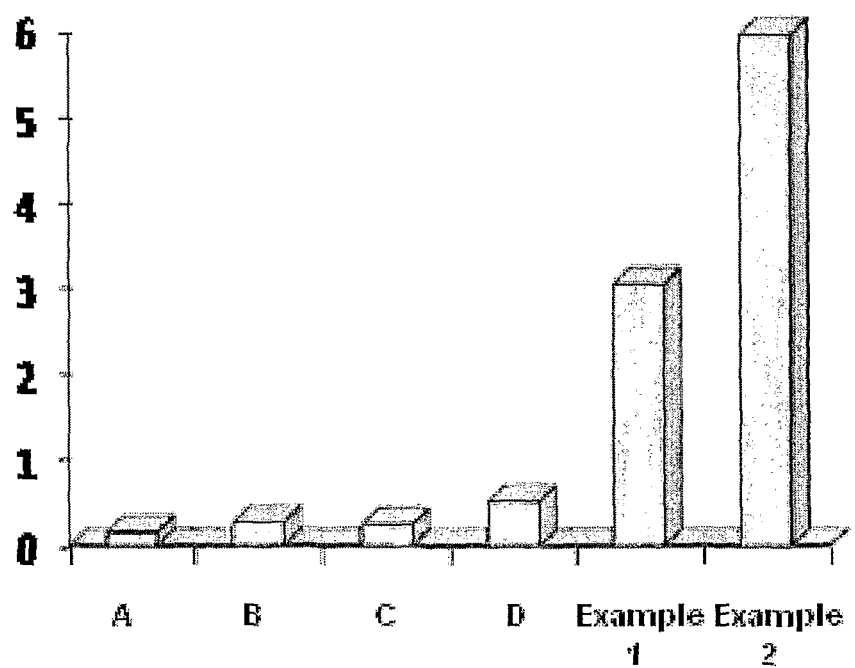
FIG. 2 depicts the synergistic antiviral activity of formulations from Example 1 and Example 2 tested for their antiviral activity against Vaccinia virus after 60 seconds exposure in comparison to compositions A,B,C and D containing ethanol 25% only, 0.1% sodium docusate in 25% ethanol, 0.1% geraniol in 25% ethanol and 0.2% menthol in 25% respectively.

The present invention is predicated, at least in part, on the surprising and unexpected discovery that the combination of one or more alcohols, geraniol, and docusate, optionally in combination with menthol, synergistically exhibits strong antiviral and antimicrobial effects. The compositions of the present invention also can include water, one or more phospholipids, one or more glycols, or a combination thereof. The compositions of the present invention exhibit highly efficient antiviral properties and may be applied topically.

Preferred alcohols include short chain volatile alcohols or $C_1$-$C_4$ alcohols such as, for example, ethanol, isopropanol (IPA), n-propanol, butanol, isobutanol or combinations thereof. Unless indicated otherwise, the term "alcohol" as used herein means one or more short chain volatile or $C_1$-$C_4$ alcohols such as, for example, ethanol, isopropanol (IPA), n-propanol, butanol, isobutanol or a combination thereof, and more particularly ethanol, isopropanol or a combination thereof, and especially ethanol. Preferred alcohols in the compositions of the present invention include ethanol, isopropanol, or a combination thereof, with ethanol being the more preferred alcohol. The ethanol (or ethyl alcohol) to be used in the compositions of this invention may be of any suitable grade, including commercial grade 95% ethyl alcohol, although some compositions described in the Examples have been prepared using (for convenience) absolute alcohol.

Preferred glycols include one or more short chain glycols such as, for example, ethylene glycol, diethylene glycol, propylene glycol, tetraglycol, butylene glycol, pentylene glycol, hexylene glycol, ethers thereof, for example diethylene glycol monomethyl ether, and combinations of any of the foregoing. Unless indicated otherwise, the term "glycol" as used herein means one or more short chain glycols as described herein, especially propylene glycol.

Unless indicated otherwise, the term "phospholipid" as described herein refers to an amphipathic compound that includes a lipid to which one or more phosphate groups are attached. Phospholipids that can be used in the compositions of the invention can include, e.g., commercially available phospholipids and other phospholipids that are known in the art. Suitable phospholipids can include, for example, lecithin, cephalin, phosphatidylcholine (PC), phosphatidylethanolamine, phosphatidylinositol, phosphatidylserine, and the like, and combinations thereof. Soy phospholipids such as the Phospholipon products (e.g., Phospholipon 90G) have been found to be especially effective in some embodiments. Other suitable Phospholipons can include, e.g., Phospholipon 85 and Phospholipon 100, and saturated chain phospholipids, e.g., Phospholipon 90H.

The term "docusate" or "docusate salt" refers to a salt of dioctyl sulfosuccinic acid. Examples of docusates or docusate salts include sodium, potassium or calcium dioctyl sulfosuccinate. A preferred docusate salt is sodium docusate.

Geraniol or 3,7-dimethylocta-2,6-dien-1-ol is a monoterpenoid alcohol of formula $C_9H_{15}CH_2OH$ is a known compound that may be prepared synthetically or isolated from natural sources such as, for example, essential oils, e.g., from the oil of geranium. Various isomers are possible, with the 2E isomer being most common.

Menthol or 5-methyl-2-(1-methylethyl) cyclohexanol is a substituted cyclohexyl alcohol of formula $CH_3C_6H_9(C_3H_7)$ OH, and is a known compound, which may be obtained from natural sources such as, for example, various mint oils, or may be produced synthetically. Various isomers are possible, with the 1-isomer being the most common.

An "effective amount" of actives in the instant compositions means an amount, which is effective at the concentrations used to inactivate or at least substantially reduce the counts of microorganisms such as, for example, bacteria, viruses and/or fungi. A composition is generally considered highly effective whenever it kills or substantially reduces the counts of microorganisms such as, for example, bacteria, viruses and/or fungi. The compositions of the present invention can reduce the counts of one or more microorganisms from the above classes to, for example, ⅒, 1/100, or 1/1000 or less of their initial counts.

The compositions of the present invention can be used for sanitizing and/or disinfecting hands, skin, mouth cavity, lips, mucosae, surfaces, food contact surfaces, instruments, food and fruit, skin and skin appendages.

In one embodiment, the compositions of this invention comprise ethanol, docusate, geraniol, and, optionally, menthol. In another embodiment, the compositions of the invention comprise ethanol, docusate, geraniol, water, propylene glycol, and, optionally, menthol.

Another embodiment of the present invention provides a sanitizing composition for hands, skin, mouth cavity, lips, mucosae, surfaces, food contact surfaces, instruments, food and fruit, skin and skin appendages, comprising combinations of effective amounts of docusate, alcohol, geraniol, and at least one additional active, which may include menthol.

The compositions of the invention may further comprise a phospholipid, water, a glycol and, optionally, at least one additional antimicrobial, antiviral or antifungal agent, or a combination thereof.

The concentrations of volatile or $C_1$-$C_4$ alcohol in the compositions of the present invention can include, but are not limited to, for example, concentrations in ranges of from about 7 wt % to about 85 wt %, e.g., from about 15 wt % to about 85 wt %, of one or more of such alcohols. Exemplary concentrations of volatile or $C_1$-$C_4$ alcohol in the compositions of the invention include, but are not limited to, for example, concentrations in ranges of from about 7 wt % to about 70 wt %, from about 7 wt % to about 65 wt %, from about 7 wt % to about 60 wt %, from about 7 wt % to about 55 wt %, from about 7 wt % to about 50 wt %, from about 7 wt % to about 45 wt %, from about 7 wt % to about 40 wt %, from about 7 wt % to about 35 wt %, from about 7 wt % to about 30 wt %, from about 7 wt % to about 25 wt %, from about 7 wt % to about 20 wt %, from about 7 wt % to about 15 wt %, from about 10 wt % to about 70 wt %, from about 10 wt % to about 65 wt %, from about 10 wt % to about 60 wt %, from about 10 wt % to about 55 wt %, from about 10 wt % to about 50 wt %, from about 10 wt % to about 45 wt %, from about 10 wt % to about 40 wt %, from about 10 wt % to about 35 wt %, from about 10 wt % to about 30 wt %, from about 10 wt % to about 25 wt %, from about 10 wt % to about 20 wt %, from about 10 wt % to about 15 wt %, from about 12 wt % to about 70 wt %, from about 12 wt % to about 65 wt %, from about 12 wt % to about 60 wt %, from about 12 wt % to about 55 wt %, from about 12 wt % to about 50 wt %, from about 12 wt % to about 45 wt %, from about 12 wt % to about 40 wt %, from about 12 wt % to about 35 wt %, from about 12 wt % to about 30 wt %, from about 12 wt % to about 25 wt %, from about 12 wt % to about 20 wt %, from about 12 wt % to about 15 wt %, from about 15 wt % to about 70 wt %, from about 15 wt % to about 65 wt %, from about 15 wt % to about 60 wt %, from about 15 wt % to about 55 wt %, from about 15 wt % to about 50 wt %, from about 15 wt % to about 45 wt %, from about 15 wt % to about 40 wt %, from about 15 wt % to about 35 wt %, from about 15 wt % to about 30 wt %, from about 15 wt % to about 25 wt %, from about 15 wt % to about 20 wt %, from about 20 wt % to about 70 wt %, from about 20 wt % to about 65 wt %, from about 20 wt % to about 60 wt %, from about 20 wt % to about 55 wt %, from about 20 wt % to about 50 wt %, from about 20 wt % to about 45 wt %, from about 20 wt % to about 40 wt %, from about 20 wt % to about 35 wt %, from about 20 wt % to about 30 wt %, from about 20 wt % to about 25 wt %, from about 25 wt % to about 70 wt %, from about 25 wt % to about 65 wt %, from about 25 wt % to about 60 wt %, from about 25 wt % to about 55 wt %, from about 25 wt % to about 50 wt %, from about 25 wt % to about 45 wt %, from about 25 wt % to about 40 wt %, from about 25 wt % to about 35 wt %, from about 25 wt % to about 30 wt %, from about 30 wt % to about 70 wt %, from about 30 wt % to about 65 wt %, from about 30 wt % to about 60 wt %, from about 30 wt % to about 55 wt %, from about 30 wt % to about 50 wt %, from about 30 wt % to about 45 wt %, from about 30 wt % to about 40 wt %, from about 30 wt % to about 35 wt %, from about 35 wt % to about 70 wt %, from about 35 wt % to about 65 wt %, from about 35 wt % to about 60 wt %, from about 35 wt % to about 55 wt %, from about 35 wt % to about 50 wt %, from about 35 wt % to about 45 wt %, from about 35 wt % to about 40 wt %, from about 40 wt % to about 70 wt %, from about 40 wt % to about 65 wt %, from about 40 wt % to about 60 wt %, from about 40 wt % to about 55 wt %, from about 40 wt % to about 50 wt %, from about 40 wt % to about 45 wt %, from about 45 wt % to about 70 wt %, from about 45 wt % to about 65 wt %, from about 45 wt % to about 60 wt %, from about 45 wt % to about 55 wt %, and from about 45 wt % to about 50 wt %. The volatile or $C_1$-$C_4$ alcohol used within these ranges preferably includes ethanol, isopropanol, or a mixture thereof, and most preferably ethanol. Exemplary concentration ranges of volatile or $C_1$-$C_4$ alcohol include 20-70 wt % ethanol, isopropanol, or a mixture thereof, 15-65 wt % ethanol, isopropanol, or a mixture thereof, 20-65 wt % ethanol, isopropanol, or a mixture thereof, 15-55 wt % ethanol, isopropanol, or a mixture thereof, and 12-50 wt % ethanol, isopropanol, or a mixture thereof.

Concentrations of docusate salt(s) in the compositions of the invention can include, but are not limited to, for example, docusate salt concentrations in ranges of from about 0.01 wt % to about 2 wt %, from about 0.05 wt % to about 2 wt %, from about 0.1 wt % to about 2 wt %, from about 0.2 wt % to about 2 wt %, from about 0.3 wt % to about 2 wt %, from about 0.4 wt % to about 2 wt %, from about 0.5 wt % to about 2 wt %, from about 0.01 wt % to about 1 wt %, from about 0.05 wt % to about 1 wt %, from about 0.1 wt % to about 1 wt %, from about 0.2 wt % to about 1 wt %, from about 0.3 wt % to about 1 wt %, from about 0.4 wt % to about 1 wt %, from about 0.5 wt % to about 1 wt %, from about 0.6 wt % to about 1 wt %, from about 0.7 wt % to about 1 wt %, from about 0.8 wt % to about 1 wt %, from about 0.9 wt % to about 1 wt %, from about 0.01 wt % to about 0.5 wt %, from about 0.05 wt % to about 0.5 wt %, from about 0.1 wt % to about 0.5 wt %, from about 0.2 wt % to about 0.5 wt %, from about 0.3 wt % to about 0.5 wt %, and from about 0.4 wt % to about 0.5 wt %.

Concentrations of geraniol in the compositions of the invention can include, but are not limited to, for example, geraniol concentrations in ranges of from about 0.01 wt % to about 2 wt %, from about 0.05 wt % to about 2 wt %, from about 0.1 wt % to about 2 wt %, from about 0.2 wt % to about 2 wt %, from about 0.3 wt % to about 2 wt %, from about 0.4 wt % to about 2 wt %, from about 0.5 wt % to about 2 wt %, from about 0.01 wt % to about 1 wt %, from about 0.05 wt % to about 1 wt %, from about 0.1 wt % to about 1 wt %, from about 0.2 wt % to about 1 wt %, from about 0.3 wt % to about 1 wt %, from about 0.4 wt % to about 1 wt %, from about 0.5 wt % to about 1 wt %, from about 0.6 wt % to about 1 wt %, from about 0.7 wt % to about 1 wt %, from about 0.8 wt % to about 1 wt %, from about 0.9 wt % to about 1 wt %, from about 0.01 wt % to about 0.5 wt %, from about 0.05 wt % to about 0.5 wt %, from about 0.1 wt % to about 0.5 wt %, from about 0.2 wt % to about 0.5 wt %, from about 0.3 wt % to about 0.5 wt %, and from about 0.4 wt % to about 0.5 wt %.

If included, concentrations of menthol in the compositions of the invention can include, but are not limited to, for example, menthol concentrations in ranges of from about 0.01 wt % to about 2 wt %, from about 0.05 wt % to about 2 wt %, from about 0.1 wt % to about 2 wt %, from about 0.2 wt % to about 2 wt %, from about 0.3 wt % to about 2 wt %, from about 0.4 wt % to about 2 wt %, from about 0.5 wt % to about 2 wt %, from about 0.01 wt % to about 1 wt %, from about 0.05 wt % to about 1 wt %, from about 0.1 wt % to about 1 wt %, from about 0.2 wt % to about 1 wt %, from about 0.3 wt % to about 1 wt %, from about 0.4 wt % to about 1 wt %, from about 0.5 wt % to about 1 wt %, from about 0.6 wt % to about 1 wt %, from about 0.7 wt % to about 1 wt %, from about 0.8 wt % to about 1 wt %, from about 0.9 wt % to about 1 wt %, from about 0.01 wt % to about 0.5 wt %, from about 0.05 wt % to about 0.5 wt %, from about 0.1 wt % to about 0.5 wt %, from about 0.2 wt % to about 0.5 wt %, from about 0.3 wt % to about 0.5 wt %, and from about 0.4 wt % to about 0.5 wt %.

In some embodiments, the presence of water may optimize antimicrobial efficacy. If included, concentrations of water in the compositions of the invention can include, for example, water concentrations in ranges of from about 10 wt % to about 85 wt %, e.g., from about 15 wt % to about 85 wt %. Exemplary water concentrations that can be used in the compositions of the present invention include from about 10 wt % water to about 85 wt % water, from about 10 wt % water to about 80 wt % water, from about 10 wt % water to about 75 wt % water, from about 10 wt % water to about 70 wt % water, from about 10 wt % water to about 65 wt % water, from about 10 wt % water to about 60 wt % water, from about 10 wt % water to about 55 wt % water, from about 10 wt % water to about 50 wt % water, from about 10 wt % water to about 45 wt % water, from about 10 wt % water to about 40 wt % water, from about 10 wt % water to about 35 wt % water, from about 10 wt % water to about 30 wt % water, from about 10 wt % water to about 25 wt % water, from about 10 wt % water to about 20 wt % water, from about 10 wt % water to about 15 wt % water, from about 15 wt % water to about 85 wt % water, from about 15 wt % water to about 80 wt % water, from about 15 wt % water to about 75 wt % water, from about 15 wt % water to about 70 wt % water, from about 15 wt % water to about 65 wt % water, from about 15 wt % water to about 60 wt % water, from about 15 wt % water to about 55 wt % water, from about 15 wt % water to about 50 wt % water, from about 15 wt % water to about 45 wt % water, from about 15 wt % water to about 40 wt % water, from about 15 wt % water to about 35 wt % water, from about 15 wt % water to about 30 wt % water, from about 15 wt % water to about 25 wt % water, from about 15 wt % water to about 20 wt % water, from about 20 wt % water to about 85 wt % water, from about 20 wt % water to about 80 wt % water, from about 20 wt % water to about 75 wt % water, from about 20 wt % water to about 70 wt % water, from about 20 wt % water to about 65 wt % water, from about 20 wt % water to about 60 wt % water, from about 20 wt % water to about 55 wt % water, from about 20 wt % water to about 50 wt % water, from about 20 wt % water to about 45 wt % water, from about 20 wt % water to about 40 wt % water, from about 20 wt % water to about 35 wt % water, from about 20 wt % water to about 30 wt % water, from about 20 wt % water to about 25 wt % water, from about 25 wt % water to about 85 wt % water, from about 25 wt % water to about 80 wt % water, from about 25 wt % water to about 75 wt % water, from about 25 wt % water to about 70 wt % water, from about 25 wt % water to about 65 wt % water, from about 25 wt % water to about 60 wt % water, from about 25 wt % water to about 55 wt % water, from about 25 wt % water to about 50 wt % water, from about 25 wt % water to about 45 wt % water, from about 25 wt % water to about 40 wt % water, from about 25 wt % water to about 35 wt % water, from about 25 wt % water to about 30 wt % water, from about 30 wt % water to about 85 wt % water, from about 30 wt % water to about 80 wt % water, from about 30 wt % water to about 75 wt % water, from about 30 wt % water to about 70 wt % water, from about 30 wt % water to about 65 wt % water, from about 30 wt % water to about 60 wt % water, from about 30 wt % water to about 55 wt % water, from about 30 wt % water to about 50 wt % water, from about 30 wt % water to about 45 wt % water, from about 30 wt % water to about 40 wt % water, from about 30 wt % water to about 35 wt % water, from about 35 wt % water to about 85 wt % water, from about 35 wt % water to about 80 wt % water, from about 35 wt % water to about 75 wt % water, from about 35 wt % water to about 70 wt % water, from about 35 wt % water to about 65 wt % water, from about 35 wt % water to about 60 wt % water, from about 35 wt % water to about 55 wt % water, from about 35 wt % water to about 50 wt % water, from about 35 wt % water to about 45 wt % water, from about 35 wt % water to about 40 wt % water, from about 40 wt % water to about 85 wt % water, from about 40 wt % water to about 80 wt % water, from about 40 wt % water to about 75 wt % water, from about 40 wt % water to about 70 wt % water, from about 40 wt % water to about 65 wt % water, from about 40 wt % water to about 60 wt % water, from about 40 wt % water to about 55 wt % water, from about 40 wt % water to about 50 wt % water, from about 40 wt % water to about 45 wt % water, from about 45 wt % water to about 85 wt % water, from about 45 wt % water to about 80 wt % water, from about 45 wt % water to about 75 wt % water, from about 40 wt % water to about 70 wt % water, from about 45 wt % water to about 65 wt % water, from about 45 wt % water to about 60 wt % water, from about 45 wt % water to about 55 wt % water, from about 45 wt % water to about 50 wt % water, from about 50 wt % water to about 85 wt % water, from about 50 wt % water to about 80 wt % water, from about 50 wt % water to about 75 wt % water, from about 50 wt % water to about 70 wt % water, from about 50 wt % water to about 65 wt % water, from about 50 wt % water to about 60 wt % water, and from about 50 wt % water to about 55 wt % water.

In some embodiments, the compositions of the present invention comprise a docusate salt, geraniol, ethanol, water, a phospholipid, and, optionally, a glycol.

In other embodiments, the compositions of the present invention comprise a docusate salt, geraniol, menthol, ethanol, water, a phospholipid, and, optionally, a glycol.

The compositions of the present invention may further comprise an acid.

The compositions of the present invention may be adjusted to any suitable pH, e.g., a pH range of about 3-9.5, a pH range of about 3-8.5, e.g., from about pH 3.0 to about pH 8.5, from about pH 3.0 to about pH 8.0, from about pH 3.0 to about pH 7.5, from about pH 3.0 to about pH 7.0, from about pH 3.0 to about pH 6.5, from about pH 3.0 to about pH 6.0, from about pH 3.0 to about pH 5.5, from about pH 3.0 to about pH 5.0, from about pH 3.0 to about pH 4.5, from about pH 3.0 to about pH 4.0, from about pH 4.0 to about pH 8.5, from about pH 4.0 to about pH 8.0, from about pH 4.0 to about pH 7.5, from about pH 4.0 to about pH 7.0, from about pH 4.0 to about pH 6.5, from about pH 4.0 to about pH 6.0, from about pH 4.0 to about pH 5.5, from about pH 4.0 to about pH 5.0, from about pH 4.0 to about pH 4.5, from about pH 5.0 to about pH 8.5, from about pH 5.0 to about pH 8.0, from about pH 5.0 to about pH 7.5, from about pH 5.0 to about pH 7.0, from about pH 5.0 to about pH 6.5, from about pH 5.0 to about pH 6.0, from about pH 5.0 to about pH 5.5, from about pH 6.0 to about pH 8.5, from about pH 6.0 to about pH 8.0, from about pH 6.0 to about pH 7.5, from about pH 6.0 to about pH 7.0, from about pH 6.0 to about pH 6.5. In some embodiments, the compositions of the present invention have a pH of about 4. In other embodiments, the compositions of the present invention have a pH of about 8.5.

The compositions of the present invention may comprise one or more other additional agents such as, for example, water insoluble non-cationic antimicrobial agents, e.g., one or more halogenated diphenyl ethers, phenolic compounds including, e.g., phenol and its homologs, mono and polyalkyl and aromatic halophenols, resorcinol and its derivatives, bisphenolic compounds, halogenated salicylanilides, benzoic esters, halogenated carbanilides, and the like, or a combination of any of the foregoing. The water soluble antimicrobials can include, for example, quaternary ammonium, bis-biguanide salts, and triclosan monophosphate. The quaternary ammonium agents can include those in which one or two of the substituents on the quaternary nitrogen has a carbon chain length (typically an alkyl group) from about 8 to about 20, e.g., from about 10 to about 18 carbon atoms, while the remaining substituents (typically alkyl or benzyl group) have a lower number of carbon atoms, such as, e.g., from 1 to about 7 carbon atoms, typically methyl, ethyl or benzyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents. Other agents can include, e.g., bis[4-(R-amino)-1-pyridinium]alkanes, cetyl pyridinium chloride, chlorhexidine, triclosan, triclosan monophosphate, benzalkonium chloride, and sodium benzoate.

Other additional agents may be 3-diol, adipic acid, alkane sulfonates, allicin, aloe barbadensis, aloe barbadensis leaf juice, alpha-glucan-oligosaccharide, ammonium iodide, bacteriophages, benzalkonium chloride, benzoic acid, benzyl alcohol, bromochlorophene 2-bromo-2-nitropropane-1, butylglucoside caprate, butylparaben, caprylic/capric glycerides, capryloyl collagen amino acids, capryloyl glycine, capryloyl keratin amino acids, captan, cationic oligomer, cetethyldimonium bromide, cetyl pyridinium chloride, chaotropic agent, chlorhexidine, chlorhexidine diacetate, chlorhexidine digluconate, chlorhexidine dihydrochloride, chlorothymol, chloroxylenol, chlorphenesin, citral, citric acid, citron oil, copper pca, dicarboxylic acid, dichlorobenzyl alcohol, dilauryldimonium chloride, docosanol, domiphen bromide, eicosanol, ethylparaben, eucalyptol, eucalyptus globulus extract, oli, fennel (foeniculum vulgare) extract, garlic (allium sativum) extract, gentian violet, geranium oil, glutaric acid, glyceric acid, glyceryl caprylate, glyceryllaurate, guanidine HCl, hexamidine diisothionate, hexetidine, hinokitiol, honeysuckle (lonicera caprifolium) extract, honeysuckle (lonicera japonica) extract, hydrochloric acid, hydrogen peroxide, iceland moss (cetraria islandica) extract, iodine, lactic acid, lactoferrin, lauralkonium bromide, lauralkonium chloride, laurtrimonium chloride, laurylpyridinium chloride, leptospermum scoparium oil, lichen (usnea barbata) extract, maleic acid, malic acid, methyl salicylate, methylparaben, mushroom (cordyceps sabolifera) extract, myristalkonium chloride, nitric acid, o-phenylphenol, orange (citrus aurantium dulcis) peel extract, orange (citrus sinensis) flower extract, peg-42 ebiriko ceramides extract, pentylene glycol, peppermint (mentha piperita) extract, peppermint oil, pfaffia paniculata extract, phenethyl alcohol, phenol, phenoxyethanol, phenoxyisopropanol, phenyl mercuric acetate, phenyl mercuric benzoate, phenyl mercuric borate, philodendron (phellodendron amurense) extract, phosphoric acid, phytosphingosine, pine (pinus sylvestris) needle extract, piroctone olamine, polymethoxy bicyclic oxazolidine, polyquatemium-22, polyquatemium-37, polyquaternium polymer, potassium sorbate, propylparaben, quaternium 73, ricinoleamodopropyltrimonium ethosulfate, rubus thunbergii extract, sage (salvia officinalis) extract, sodium benzoate, sodium pyrithione, sodium ricinoleate, sodium shale oil sulfonate, sodium usnate, succinic acid, tea tree (melaleuca alternifolia) oil, thimerosal, thiocyanic acid salts, thiourea, thyme (thymus vulgaris) extract, thymol, tocopheryl acetate, triclocarban, triclosan, undecylenamidopropyltrimonium methosulfate, undecylenic acid, urea, zinc oxide, zinc pca, zinc pyrithione, zinc undecylenate, and the like, and suitable combinations thereof.

In some embodiments, the composition of the present invention is effective in killing gram negative and gram positive bacteria, parasites and enveloped viruses. More specifically in certain embodiments the sanitizing composition has a rapid antibacterial efficacy against gram positive bacteria such as *staphylococcus* and against gram negative bacteria such as *Pseudomonas*. In these or other embodiments, the composition of the present invention has a rapid efficacy against fungi such as *Candida*. In one or more embodiments, the composition of the present invention exhibits efficacy against enveloped viruses such as herpes, influenza and vaccinia.

In some embodiments, the composition of the present invention exhibits efficacy against nonenveloped viruses including members of the families Picornaviridae, Reoviridae, Caliciviridae, Adenoviridae and Parvoviridae. More specifically, in certain embodiments, the composition of the present invention exhibits antiviral efficacy against nonenveloped viruses such as rhinovirus, poliovirus, adenovirus, norovirus, papillomavirus, feline calicivirus, hepatitis A virus, parvovirus, and rotavirus.

In some embodiments, the sanitizing composition is brought into contact with the virus particles, and greater than 1 log kill is achieved in less than 60 seconds, in another embodiment greater than 2 log kill is achieved in less than 60 seconds, and in yet another embodiment, greater than 3 log kill is achieved in less than 60 seconds. In another embodiment, greater than 3.5 log kill is achieved in less than 60 seconds, and in yet another embodiment, greater than 4 log kill is achieved in less than 60 seconds. In one or more embodiments, the virus is completely inactivated to the limits of detection, based on the test method employed, within about 60 seconds.

In some embodiments, the composition of the present invention exhibits efficacy against Influenza viruses including, e.g., Influenza virus H1N1, 2009 Influenza A virus, and Swine Influenza H1N1.

In one embodiment there are provided sanitizing compositions comprising alcohol, sodium docusate and geraniol exhibiting highly efficient antiviral properties.

In another embodiment there are provided sanitizing compositions comprising alcohol, sodium docusate, geraniol and menthol exhibiting highly efficient antiviral properties.

In yet another embodiment there are provided sanitizing compositions comprising, alcohol, sodium docusate, geraniol, and, optionally, menthol exhibiting highly efficient antiviral properties against non enveloped viruses In yet another embodiment there are provided sanitizing compositions comprising alcohol, sodium docusate and geraniol, which exhibit highly efficient sanitizing properties against microorganisms such as, e.g., bacteria, viruses and fungi.

In another embodiment there are provided sanitizing compositions comprising alcohol, sodium docusate, geraniol and menthol exhibiting highly efficient sanitizing properties against microorganisms like bacteria, viruses and fungi.

In one embodiment there are provided sanitizing compositions comprising, alcohol, geraniol, menthol and optionally glycol and/or phospholipid exhibiting highly efficient sanitizing properties against microorganisms like bacteria, viruses and fungi.

In one embodiment there are provided sanitizing compositions comprising, alcohol, sodium docusate, geraniol, and, optionally, menthol, a glycol, a phospholipid, or a combination of at least two of these optional components, exhibiting highly efficient sanitizing properties against non-enveloped viruses.

In another embodiment there are provided sanitizing compositions comprising alcohol, sodium docusate, geraniol, menthol, and, optionally, a glycol and/or a phospholipid, exhibiting a highly efficient sanitizing properties against non-enveloped viruses.

In one embodiment there are provided sanitizing compositions comprising, alcohol, sodium docusate, and geraniol exhibiting a synergistic effect against viruses.

In one embodiment there are provided sanitizing compositions comprising alcohol, sodium docusate, geraniol, and menthol exhibiting a synergistic effect against viruses.

In one embodiment there are provided sanitizing compositions comprising alcohol, sodium docusate, geraniol, and, optionally, menthol exhibiting a synergistic effect against nonenveloped viruses.

In one embodiment there are provided sanitizing compositions comprising alcohol, sodium docusate, and geraniol exhibiting a synergistic effect against microorganisms like bacteria, viruses and fungi.

In another embodiment there are provided sanitizing compositions comprising alcohol, sodium docusate, geraniol, and menthol exhibiting a synergistic effect against microorganisms like bacteria, viruses and fungi.

In one embodiment there are provided sanitizing compositions comprising, alcohol, geraniol, menthol, and, optionally, a glycol and/or a phospholipid exhibiting a synergistic effect against microorganisms like bacteria, viruses and fungi.

In one embodiment there are provided sanitizing compositions comprising, alcohol, sodium docusate, geraniol, and, optionally, menthol, a glycol, a phospholipid, or a combination of at least two of these optional components, exhibiting a synergistic effect against non enveloped viruses.

In another embodiment there are provided sanitizing compositions comprising alcohol, sodium docusate, geraniol, menthol, and, optionally, a glycol and/or a phospholipid, exhibiting a synergistic effect against non enveloped viruses In one embodiment there are provided methods of inactivating enveloped viruses and nonenveloped viruses, the method comprising: contacting one or more surfaces contaminated with one or more of such viruses with a sanitizing composition comprising, alcohol, sodium docusate and geraniol, which optionally may further comprise menthol, a glycol, a phospholipid, or a combination of at least two of these optional components.

In another embodiment there are provided methods of killing gram positive, gram negative bacteria and fungus, the method comprising: contacting surfaces contaminated with said bacteria or fungus with a sanitizing composition comprising alcohol, water, sodium docusate, and geraniol, which optionally may further comprise menthol, a glycol, a phospholipid, or a combination of at least two of these optional components.

In another embodiment there are provided sanitizing compositions comprising alcohol, sodium docusate, geraniol, and, optionally, menthol, a glycol, a phospholipid, or a combination of at least two of these optional components, exhibiting sanitizing residual and prolong effect.

In another embodiment, there is provided an article of manufacture, comprising a container containing a sanitizing and disinfecting composition and instructions for using the composition, said instructions detailing how to apply the sanitizing and disinfecting composition to skin, spray or rub or massage the composition onto the skin one or more times a day, according to need.

One important feature of this invention is that the compositions of this invention comprise GRAS ingredients listed in the FDA's EAFUS database allowing their use by food service providers, healthcare personnel, consumers and children.

Another important feature of this invention is that the compositions of this invention comprise GRAS ingredients, allowing their use in mouthwashes, oral care, hand sanitizing and food surfaces sanitizers.

Compositions of this invention exhibiting very good compatibility with skin, are non-irritating, non-sticky, quick drying and exhibiting efficient activity against microorganisms like bacteria, viruses and fungi in spite of a relative low concentrations of ethanol, preferably comprise: 15-60% w/w ethanol, 0-30% w/w propylene glycol, 0.01-1% w/w docusate salt, 0.01-1% w/w geraniol and 0.01-1% w/w menthol, carbopol, neutralizer and water.

Preferably, compositions exhibiting very good compatibility with skin, are non-irritating, non-sticky, quick drying and exhibiting efficient activity against microorganisms like bacteria, viruses and fungi in spite of a relative low concentration of ethanol comprise: 15-60% w/w ethanol, 0-30% w/w propylene glycol, 0.01-1% w/w docusate salt, 0.1-15% phospholipid, 0.01-1% w/w geraniol, 0.01-1% w/w menthol, 0.1-1% w/w Vitamin E, carbopol, neutralizer and water.

One preferred composition found to have very good compatibility with skin, being non-irritating, non-sticky, quick drying as well as exhibiting efficient activity against microorganisms like bacteria, viruses and fungi in spite of a relative low concentration of ethanol comprises: 50% w/w ethanol, 0.1% w/w sodium docusate, 0.1% w/w geraniol, 0.2% w/w menthol, 0.2% w/w vitamin E, 20% w/w propylene glycol, 0.5% w/w phospholipid, carbopol, neutralizer and water.

The composition rapidly and efficiently decreases the microbial, fungal and viral populations when applied on the surface, human or animal skin, tissues or mucosa. Moreover, the sanitizing composition is not damaging to the skin or mucosa and is not drying the skin even after multiple applications. The compositions further are quick drying and are not sticky to the skin. As an added benefit, the compositions of the present invention may further provide a moisturizing property to the skin.

One composition of the present invention is for inactivating viruses and microorganisms in a mouthwash comprises 25% w/w ethanol, 0.1% w/w sodium docusate, 0.1% w/w geraniol, 0.2% w/w menthol and water. These compositions may further comprise sodium benzoate, sorbitol, eucalyptol, thymol, terpenes, lipophilic surfactant, lipophilic surfactant with HLB 1-10, Arlacels, glyceryl esters spans, sorbitan esters, oils, isopropyl myristate, cetylpyridinium chloride, triclosan, methyl salicylate, hexetidine, fluorides, colors, chlorhexidine gluconate, hydrogen peroxide, domiphen bromide, xylitol, sodium saccharine or other sweeteners.

Compositions of the present invention for inactivating viruses and microorganisms as mouthwashes preferably comprise 10-25% w/w ethanol, 0.05-0.3% w/w sodium docusate, 0.05-0.3% w/w geraniol, 0.01-0.3% w/w menthol, water. These compositions may further comprise sodium benzoate, sorbitol, eucalyptol, thymol, terpenes, lipophilic surfactant, lipophilic surfactant with HLB 1-10, Arlacels, spans, glyceryl esters, sorbitan esters, oils, isopropyl myristate, cetylpyridinium chloride, triclosan, methyl salicylate, hexetidine, fluorides, colors and pigments, chlorhexidine gluconate, hydrogen peroxide, domiphen bromide, xylitol, sodium saccharine or other sweeteners.

Compositions of the present invention which may be applied on the lips for inactivating viruses and microorganisms preferably comprise 7-25% w/w ethanol, 0.01-0.3% w/w sodium docusate, 0.01-0.3% w/w geraniol, 0.01-0.3% w/w menthol, 0-20% w/w propylene glycol, 0.1-20% w/w soy phospholipid and water. This composition may further comprise glycerol, cholesterol, sorbitol and vitamin E.

One preferred composition of the present invention to be applied on the lips for inactivating viruses and microorganisms comprises 25% w/w ethanol, 0.05% w/w sodium docusate, 0.1% w/w geraniol, 0.2% w/w menthol, 20% w/w propylene glycol, 15% w/w soy phospholipid and water. This composition may further comprise glycerol, cholesterol, sorbitol and vitamin E.

The composition may be applied once or repeatedly and frequently depending upon the level of sanitization desired, e.g., the degree of residual microbial or viral contamination, if any.

The composition for topical use of this invention may include other ingredients. Certain ingredients such as organic and inorganic salts may also be incorporated. The composition may additionally include compounds selected from coloring agents, antimicrobial, antiviral or antifungal agents, antioxidants, fragrances, preservatives, buffers, acids, polymers, essential oils, terpenes, eucalyptol, thymol, thickeners, moisturizing agents, plant extracts, gel forming agents, neutralizers, rubificients, emollients, silicones, detackifying agents, vitamins, nutritive agents as well as any combination of the above.

Optionally, emollients and aesthetic additives, such as fragrance and/or colorants may also be added to the sanitizing hand cleanser formulation. Emollients or moisturizing agents, fragrance and colorants may be added as necessary and at concentrations suitable for consumer acceptance. The formulation may also include additional emollients, essential oils, herbal materials or a combination thereof, added to the compositions to further aid skin moisturization.

Non-limiting examples of preservatives include but are not limited to sodium benzoate, benzoic acid, sorbitol, phenoxyethanol, phenylethyl alcohol, benzalkonium chloride, EDTA, benzyl alcohol, potassium sorbate, parabens, chlorhexidine gluconate, and mixtures thereof as described in Martindale "The Complete Drug Reference", 36th Edition by Sean C. Sweetman, Mar. 16, 2009 and "CTFA Cosmetic Ingredient Handbook and Supplement" by John A. Wenninger and Gerald N. McEwen June 1992, included herein in their entirety by reference.

Optionally, the compositions of the present invention may include viscosity increasing agents to thicken the composition. These viscosity increasing agents may include gelling agents, naturally-occurring polymeric materials, hydrophilic gelling agents, cellulose derivative, chitan, chitosan, hydroxypropyl cellulose derivatives.

Optionally, detackifying agents may be added to the compositions of the present invention at an effective amount to reduce the stickiness or tack associated with humectants and/or gelling agents.

Optionally, suitable humectants agents may be added to the composition of the present invention. These include polyhydric alcohols such as glycerin, sorbitol, xylitol, butylene glycol, polyethylene glycol, propylene glycol and trimethyl glycine.

The compositions of the present invention preferably exhibit antiviral, antibacterial, antifungal, anti-yeast, and anti mold activities, both immediate and residual. The compositions of the present invention may be suitable for a variety of uses.

In an embodiment of this invention, there are provided methods of treatment by the exposure of the contaminated surfaces to the compositions of this invention for a number of afflictions and conditions including, but certainly are not limited to, the inactivation of viruses, bacteria, fungi, yeasts and molds, the prevention of contamination from viral or and microbial infections, the prevention of infection by common cold, flu, or associated respiratory disease in a mammal; the prevention and/or treatment or transmission of a diarrhea in a mammal; the prevention of transmission of HIV, herpes virus, papilloma virus from the oral cavity or lips, the prevention of sexually transmitted diseases, the prevention and/or treatment and/or transmission of bacteria-related diseases in mammals resulting from contact with a bacteria-infected surface; the sanitization of hard surfaces; the prevention of orally transmitted diseases, the improvement of the overall health of a mammal; the reduction of absenteeism; the prevention and/or treatment of dandruff and acne; and combinations thereof.

In an embodiment of this invention, there are provided methods of treatment by the exposure of the contaminated surfaces to the compositions of this invention of a number of afflictions and conditions including, but certainly are not limited to the prevention or treatment of gingivitis, plaque and bad breath.

In one embodiment, the compositions of this invention may be prepared as concentrated solutions or suspensions to be diluted with solvents such as water or alcohol before use.

The compositions of this invention may be used as hand sanitizing liquid, foam with or without gas and or propellant, gel, spray, lotion, solution, emulsion, cream or incorporated into woven or non-woven wipes, sponges or tissues, lipstick, roll-on or liquid lipstick.

In one embodiment, the compositions may be dispensed by a pump dispenser or container, said container having an actuator, a fluid distribution system, an automatic dispensing system, sachets, plastic bottles, jars, brushes, wipes, non-woven wipes, wet towels, bottles, sponges, cans, roll-ons, applicators, single dose containers.

The dispensing package may have a flip-top cover, a retractable cover, rotatable or removable sleeve to prevent actuation. The package may be disposable and designed for one use and not designed to be refillable. The package may be durable and suitable for refilling. The dispenser package can be refilled with a refill assembly.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

EXAMPLES

The following examples further illustrate the invention but, of course, should not be construed as in any way limiting its scope.

Example 1

|  | % w/w |
| --- | --- |
| Ethanol | 25 |
| Sodium Docusate | 0.1 |
| Geraniol | 0.1 |
| Water to | 100 |

Method of preparation for Example 1: Geraniol was added to the ethanol. A clear solution was obtained. Sodium docusate was dissolved in water by stirring. The aqueous solution was added to the ethanolic solution while mixing at 700 rpm with a Heidolph mixer.

Example 2

|  | % w/w |
| --- | --- |
| Ethanol | 25 |
| Sodium Docusate | 0.1 |
| Geraniol | 0.1 |
| Menthol | 0.2 |
| Water to | 100 |

Method of preparation: Menthol and geraniol were added to the ethanol while mixing at 700 rpm with a mixer (Heidolph). A clear solution was obtained. Sodium docusate was dissolved in water by stirring. The aqueous solution obtained was added to the ethanolic solution while mixing at 700 rpm with a mixer (Heidolph)

Example 3

|  | % w/w |
| --- | --- |
| Ethanol | 15-65 |
| Sodium Docusate | 0.1 |
| Geraniol | 0.1 |
| Menthol | 0.2 |
| Propylene Glycol | 0.5-20 |
| Water to | 100 |

Method of preparation is according to example 2. Propylene glycol is added to the ethanol phase while mixing at 700 rpm with a mixer (Heidolph).

Example 4

|  | % w/w |
| --- | --- |
| Ethanol | 15-60 |
| Isopropyl Alcohol | 0-20 |
| Sodium Docusate | 0.01-0.3 |
| Geraniol | 0.01-0.3 |
| Menthol | 0-0.3 |
| Propylene Glycol | 0-20 |
| Water to | 100 |

Method of preparation is according to example 3. Ethanol and isopropyl alcohol are mixed together at 700 rpm with a mixer (Heidolph).

Example 5

|  | % w/w |
| --- | --- |
| Ethanol | 20 |
| Sodium Docusate | 0.1 |
| Geraniol | 0.1 |
| Phospholipid | 0.5 |
| Vitamin E | 0.2 |
| Water to | 100 |

Example 6

|  | % w/w |
| --- | --- |
| Ethanol | 15-65 |
| Sodium Docusate | 0.01-0.3 |
| Geraniol | 0.01-0.3 |
| Menthol | 0-0.3 |
| Phospholipid | 0-5 |
| Propylene Glycol | 0-20 |
| Vitamin E | 0-0.5 |
| Water to | 100 |

Example 7

|  | % w/w |
| --- | --- |
| Ethanol | 50 |
| Sodium Docusate | 0.2 |
| Geraniol | 0.2 |
| Menthol | 0.1 |
| Propylene Glycol | 10 |
| Water to | 100 |

Method of preparation is according to example 3.

Example 8

|  | % w/w |
| --- | --- |
| Ethanol | 20 |
| Sodium Docusate | 0.1 |
| Geraniol | 0.15 |
| Phospholipid | 0.2 |
| Propylene Glycol | 5 |
| Vitamin E | 0.1 |
| Water to | 100 |

Example 9

|  | % w/w |
| --- | --- |
| Ethanol | 50 |
| Isopropyl Alcohol | 10 |
| Sodium Docusate | 0.5 |
| Geraniol | 0.5 |
| Menthol | 0.2 |
| Water to | 100 |

Example 10

|  | % w/w |
| --- | --- |
| Ethanol | 15 |
| Sodium Docusate | 0.1 |
| Geraniol | 0.1 |
| Menthol | 0.1 |
| Propylene Glycol | 10 |
| Carbopol (Ultrez 10) | 0.4 |
| NaOH (Sol 10%) | 0.4 |
| Sodium Benzoate | 0.1 |
| Water to | 100 |

Example 11

|  | % w/w |
| --- | --- |
| Ethanol | 60 |
| Sodium Docusate | 0.05 |
| Geraniol | 0.15 |
| Menthol | 0.2 |
| Phospholipid | 0.3 |
| Ultrez 10 | 0.4 |
| Aminomethyl propanol (AMP) | 0.8 |
| Vitamin E | 0.2 |
| Water to | 100 |

Example 12

|  | % w/w |
| --- | --- |
| Ethanol | 50 |
| Sodium Docusate | 0.1 |
| Geraniol | 0.1 |
| Menthol | 0.2 |
| Carbomer 947 | 0.4 |
| Aminomethyl propanol (AMP) | 0.8 |
| Water to | 100 |

Example 13

|  | % w/w |
| --- | --- |
| Ethanol | 50 |
| Sodium Docusate | 0.5 |
| Geraniol | 0.3 |
| Menthol | 0.3 |
| Ultrez | 0.6 |
| Aminomethyl propanol (AMP) | 1.2 |
| Water to | 100 |

Example 14

|  | % w/w |
| --- | --- |
| Ethanol | 50 |
| Sodium Docusate | 0.1 |
| Geraniol | 0.1 |
| Menthol | 0.2 |
| Phospholipon 90G | 0.5 |
| Ultrez 10 | 0.4 |
| Aminomethyl propanol (AMP) | 0.8 |
| Vitamin E | 0.2 |
| Water to | 100 |

Example 15

|  | % w/w |
| --- | --- |
| Ethanol | 50 |
| Sodium Docusate | 0.1 |
| Geraniol | 0.1 |
| Menthol | 0.2 |
| Propylene Glycol | 20 |
| Carbopol ETD 2020 | 0.4 |
| Aminomethyl propanol (AMP) | 0.8 |
| Water to | 100 |

Method of Preparation (100 g):

1. Part A:

0.4 g of Carbopol was dispersed in 15 g water by Heidolph mixer at 700 RPM. 30 g of ethanol were added with continuous mixing by Heidolph mixer.

In another container the neutralization solution was prepared by mixing 3.2 g water with 0.4 g AMP 95.

The neutralization solution was slowly added to the Carbopol mixture with continuous mixing by Heidolph mixer at 400 RPM until a gel was obtained.

2. Part B:

0.2 g menthol, 0.1 g geraniol and 20 g propylene glycol were added while mixing to 20 g ethanol.

In another container 0.1 g sodium docusate were dissolved in the remaining water. This solution was added to the ethanolic solution slowly with continuous mixing by Heidolph mixer at 700 RPM. The solution was mixed for another 5 minutes.

3.

Part B was slowly added to Part A with continuous mixing at 400 RPM.

Example 16

|  | % w/w |
| --- | --- |
| Ethanol | 50 |
| Sodium Docusate | 0.1 |
| Geraniol | 0.1 |
| Menthol | 0.2 |
| Propylene Glycol | 20 |
| Phospholipon 90G | 0.5 |
| Carbopol ETD 2020 | 0.4 |
| AMP 95 | 0.4 |
| Vitamin E | 0.2 |
| Water to | 100 |

Method of Preparation (100 g):

1. Part A:

0.4 g of Carbopol was dispersed in 15 g of Water by Heidolph mixer at 700 RPM. 30 g of Ethanol were added with continuous mixing by Heidolph mixer.

In the different container the neutralization solution was prepared by mixing 3.2 g water with 0.4 g AMP 95.

The neutralization solution was slowly added to the Carbopol mixture with continuous mixing by Heidolph mixer at 400 RPM until a gel was obtained.

2. Part B:

0.5 g Phospholipon were dissolved in 20 g ethanol. To this solution 0.2 g menthol, 0.1 g geraniol, 20 g propylene glycol and 0.2 g Vitamin E acetate were added while mixing.

In a different container 0.1 g sodium docusate were dissolved in the remaining water (xy gr). This solution was slowly added to the above ethanolic solution with continuous mixing by Heidolph mixer at 700 RPM. The solution was mixed for another 5 minutes.

3.

Part B was slowly added to Part A with continuous mixing at 400 RPM.

Example 17

|  | % w/w |
| --- | --- |
| Ethanol | 50 |
| Sodium Docusate | 0.2 |
| Geraniol | 0.2 |
| Propylene Glycol | 8 |
| Ultrez 10 | 0.4 |
| AMP | 0.8 |
| Water to | 100 |

Example 18

|  | % w/w |
| --- | --- |
| Ethanol | 60 |
| Sodium Docusate | 0.1 |
| Geraniol | 0.1 |
| Menthol | 0.2 |
| Water | 39.6 |

Example 19

| | % w/w |
|---|---|
| Ethanol | 60 |
| Sodium Docusate | 0.1 |
| Geraniol | 0.1 |
| Water to | 100 |

Example 20

| | % w/w |
|---|---|
| Ethanol | 60 |
| Sodium Docusate | 0.1 |
| Geraniol | 0.1 |
| Menthol | 0.2 |
| Phospholipon 90G | 0.5 |
| Water to | 100 |

Example 21

Mouthwash

| | % w/w |
|---|---|
| Ethanol 96 | 25 |
| Sodium Docusate | 0.05 |
| Geraniol | 0.2 |
| Menthol | 0.2 |
| Sodium Benzoate | 0.1 |
| Sorbitol | 0.0731 |
| Eucalyptol | 0.092 |
| Sodium Saccharine | q.s |
| Water to | 100 |

Method of Preparation:

Geraniol, menthol and eucalyptol were dissolved in ethanol. A clear solution was obtained.

Sodium benzoate, sorbitol and sodium docusate were dissolved in water by stirring. Sodium saccharine was added and the mixture was stirred well.

The aqueous solution was added to the above ethanolic solution while mixing at 700 rpm with a mixer (Heidolph)

Examples 22-27

Mouthwash

Composition of the Mouthwash Formulations (% w/w)

| | Example 22 | Example 23 | Example 24 | Example 25 | Example 26 | Example 27 |
|---|---|---|---|---|---|---|
| Ethanol 96 | 15 | — | 25 | 20 | 25 | 15 |
| Ethanol | — | 15 | — | — | — | — |
| Geraniol | 0.2 | 0.2 | 0.06 | 0.1 | 0.1 | 0.1 |
| Eucalyptol | 0.092 | 0.03 | 0.1 | — | 0.05 | 0.05 |
| Menthol | 0.2 | 0.2 | 0.1 | 0.092 | — | — |
| Sodium Docusate | 0.05 | 0.2 | 0.05 | 0.1 | 0.05 | 0.05 |
| Sod. Benzoate | 0.1 | 0.1 | 0.1 | 0.1 | 0.1 | 0.1 |
| Sorbitol | 0.0731 | 0.1 | 0.07 | 0.5 | 0.05 | — |
| Sweetener | — | — | qs | qs | — | qs |
| Emulsifier | qs | qs | qs | qs | qs | |
| Phospholipids | | | | | | 0.15 |
| Water | to 100 | to 100 | to 100 | to 100 | to 100 | to 100 |
| pH | 6.65 | | | | | |

Method of Preparation:

Dissolve in ethanol geraniol, menthol and other terpenes and/or phospholipids if present in the formula. A clear solution is obtained.

Dissolve sodium benzoate, sorbitol and sodium docusate in water by stirring. Add emulsifier and sweetener, if present. Stir well.

Add slowly the aqueous solution to the ethanolic solution while mixing at 700 rpm with a mixer (Heidolph)

The formulations of examples 22-27 exhibit a pH around 6, which is favorable for teeth enamel.

Example 28

Lip Sanitizing Application

| | % w/w |
|---|---|
| Ethanol 96 | 25 |
| Sodium Docusate | 0.05 |
| Geraniol | 0.2 |
| Menthol | 0.2 |
| Sun screener | qs |
| Propylene Glycol | 20 |
| Glycerin | 5 |
| Phospholipon 90G | 12 |
| Cholesterol | 0.3 |
| Eucalyptol | 0.02 |
| Vitamin E acetate | 0.5 |
| Water to | 100 |

Method of Preparation:

Geraniol, menthol, Phospholipon 90G, Vitamin E acetate and cholesterol are dissolved in ethanol by stirring (Heidolph mixer).

The sunscreen is dissolved in the above ethanolic solution after which propylene glycol is added.

Glycerin is added to the water after which sodium docusate is dissolved in the above aqueous solution by stirring.

The aqueous solution is added slowly to the ethanolic solution while mixing at 700 rpm.

Example 29

Liquid Sanitizing Lipstick

|  | % w/w |
| --- | --- |
| Ethanol 96 | 25 |
| Sodium Docusate | 0.15 |
| Geraniol | 0.1 |
| Menthol | 0.2 |
| Propylene Glycol | 20 |
| Glycerin | 5 |
| Cholesterol | 0.2 |
| Phospholipon 90H | 15 |
| Sorbitol | 0.2 |
| Vitamin E acetate | 0.5 |
| Water to | 100 |

Method of Preparation:

Geraniol, menthol, eucalyptol, Phospholipon 90H, Vitamin E acetate and cholesterol were dissolved in ethanol by stirring (Heidolph mixer) after which propylene glycol was added.

Glycerin was added to the water after which sodium docusate was dissolved in the resulting aqueous solution by stirring.

The aqueous phase was added slowly to the ethanolic phase while mixing at 700 rpm.

Examples 30-33

Sanitizing Liquid Lipstick

Formulations Composition

| Ingredient | Example 30 | Example 31 | Example 32 | Example 33 |
| --- | --- | --- | --- | --- |
|  | % w/w | | | |
| Ethanol 96 | 25 | 25 | 25 | 15 |
| Propylene glycol | 20 | 20 | 20 | 20 |
| Glycerin | 5 | 5 | 5 | 5 |
| Geraniol | 0.2 | 0.1 | 0.1 | 0.1 |
| Menthol | 0.2 | 0.2 | 0.2 | 0.092 |
| Eucalyptol | 0.092 | — | — | — |
| Cholesterol | 0.3 | 0.2 | 0.2 | — |
| Sodium Docusate | 0.05 | 0.05 | 0.05 | 0.1 |
| Lecithin | 10 | 15 | 15 | 15 |
| Vitamin E | — | 0.5 | 0.5 | 0.5 |
| Sorbitol | 0.0731 | 0.0731 | 0.0731 | 0.0731 |
| Water | 38.9849 | 33.78 | 33.8769 | 44.1349 |
| Sodium benzoate |  | 0.1 |  |  |
| Appearance | Gel | Gel | Gel | Gel, white |
| pH | 5.17 | 6.77 | 4.97 |  |

Method of Preparation:

Lecithin, Vitamin E acetate (when present), geraniol, menthol, eucalyptol (when present in the formula) and cholesterol (when present) were dissolved in ethanol by stirring (Heidolph mixer).

Sodium docusate was dissolved in the above ethanolic solution by stirring after which propylene glycol was added to the resulting solution.

Glycerol was added to the water.

The aqueous solution was slowly added to the ethanolic solution while mixing at 700 rpm.

Example 34

Hand Sanitizer

|  | % w/w |
| --- | --- |
| Ethanol | 65 |
| Sodium Docusate | 0.2 |
| Geraniol | 0.2 |
| Menthol | 0.2 |
| Phospholipid | 6 |
| Vitamin E acetate | 0.6 |
| Glycerol | 2 |
| Water to | 100 |

Method of Preparation:

Geraniol, menthol, phospholipid and Vitamin E acetate are dissolved ethanol by stirring (Heildolph mixer).

Sodium Docusate is dissolved in the above ethanolic solution by stirring.

Glycerol is added to the water.

The aqueous phase is added slowly to the ethanolic phase while mixing at 700 rpm.

Example 35

Hand Sanitizer

|  | % w/w |
| --- | --- |
| Ethanol | 62 |
| Sodium Docusate | 0.2 |
| Geraniol | 0.2 |
| Menthol | 0.2 |
| Phospholipon 90G | 5 |
| Vitamin E acetate | 0.6 |
| Propylene Glycol | 5 |
| Water to | 100 |

Method of Preparation:

Sodium docusate, geraniol, menthol, phospholipid and Vitamin E acetate were added to the ethanol by stirring (Heidolph mixer).

Propylene glycol was added to the aqueous solution.

The aqueous phase was slowly added to the ethanolic phase while mixing at 700 rpm.

Example 36

Food Surface Sanitizer

|  | % w/w |
| --- | --- |
| Ethanol | 65 |
| Sodium Docusate | 0.4 |
| Geraniol | 0.3 |
| Water to | 100 |

Example 37

Surface Sanitizer

|  | % w/w |
|---|---|
| Ethanol | 70 |
| Sodium Docusate | 1 |
| Geraniol | 0.2 |
| Menthol | 0.2 |
| Water to | 100 |

Examples 38-39

100 g of Each Composition Were Prepared

|  | B (Example 38) | C (Example 39) |
|---|---|---|
| Ethanol abs. | 60 | 60 |
| Docusate Sodium | 0.1 | 0.1 |
| Geraniol | 0.1 | 0.1 |
| (−) Menthol | 0.2 | 0.2 |
| Phospholipon 90G | — | 0.5 |
| Water | 39.6 | 39.1 |
| Appearance | Clear liquid | Clear liquid |

Method of Preparation of Example 38 and Example 39:

Docusate sodium was dissolved in water (by magnetic stirrer).

Geraniol, (−)menthol and Phospholipon 90G (if present) were dissolved in ethanol.

The aqueous solution was slowly added to the ethanolic solution while mixing continuously at 500 RPM.

Example 40

Antiviral Synergistic Effect

Formulations from Example 1 and Example 2 were tested for their antiviral activity against Vaccinia virus in comparison to comparative compositions A,B,C and D containing ethanol 25% only, 0.1% sodium docusate in 25% ethanol, 0.1% geraniol in 25% ethanol and 0.2% menthol in 25% respectively (for comparison purposes only):

Comparative Compositions

| A | Ethanol 25% |
| B | 0.1% Sod. docusate in 25% ethanol |
| C | 0.1% Geraniol in 25% ethanol |
| D | 0.2% Menthol in 25% ethanol |

Test procedure: A 1.8 ml aliquot from each formulation was mixed with 0.2 ml Vaccinia virus stock (WR strain) [obtained from NIH, Bethesda) in DMEM medium containing 2% newborn calf serum and antibiotics [Biological Industries Ltd, Bet-Haemek, Israel]. The mixture was held at room temperature (22° C.) for the specified exposure times of 30 and 60 seconds. Immediately following each exposure time, serial ten folds dilutions were made and assayed for the presence of virus. In parallel, a mixture of the virus with media only was prepared as a negative control. The virus control titer was used as a baseline to compare the percent and log reductions following exposure to the formulation from Example 1 and Example 2.

After performance of all dilutions, 0.2 ml samples of each one of the dilutions prepared from the control and test groups were used for infection of BS-C-1 (a green monkey kidney cell-line) monolayers, in 3 cm diameter dishes (Nunc, Denmark). [The cells were seeded in the dishes and incubated in a 37° C. incubator (Heraeus Instruments), supplied with 5% $CO_2$ and humidity, two to three days beforehand, in order to allow formation of confluent cell monolayers in the dishes]. After adsorption of the virus to the cells for 1 hour in the above incubator, 2 ml of a semi-solid medium Methyl Cellulose were added to each dish. The cultures were further incubated for two days when clear virus plaques were visible.

The cultures were then fixed and stained with Crystal Violet in ethanol, and virus plaques were counted. Virus titer was determined. The percentage of the inactivated virus and log reduction, following incubation with the virus, were calculated. Results are shown in Table 1, and are depicted in FIG. 1 (exposure time: 30 sec.) and FIG. 2 (exposure time: 60 sec.).

TABLE 1

$Log_{10}$ reduction of *Vaccinia Virus*

|  |  | $Log_{10}$ reduction | |
|---|---|---|---|
| Composition |  | Exposure time 30 sec | Exposure time 60 sec |
| Formulation A | Ethanol 25% | 0.2 | 0.16 |
| Formulation B | 0.1% Sod. Docusate in 25% ethanol | 1.03 | 0.7 |
| Formulation C | 0.1% Geraniol in 25% ethanol | 0.09 | 0.25 |
| Formulation D | 0.2% Menthol in 25% ethanol | 0.26 | 0.52 |
| Formulation from Example 1 | 0.1% Sodium Docusate, 0.1% Geraniol in 25% ethanol | 2.39 | 3.06 |
| Formulation from Example 2 | 0.1% Sodium Docusate, 0.1% Geraniol, 0.2% menthol in 25% ethanol | 3.53 | >6 |

Example 41

Antiviral Effect Tested Against Herpes Simplex Virus

Formulations from Example 1 and Example 2 were tested as compared to aqueous ethanol 25% alone for their antiviral activity against Herpes Simplex Virus type 1 (HF) [obtained from the Hebrew University Medical School, Jerusalem, Israel] in a similar procedure as described in Example 40 for the Vaccinia Virus.

The $log_{10}$ reductions, following incubation with the virus, were calculated.

TABLE 2

Results of $Log_{10}$ reduction of *Herpes Simplex Virus* after exposure to compositions in Example 1 and Example 2 as compared to aqueous ethanol 25% alone.

|  | $Log_{10}$ reduction | |
|---|---|---|
| Composition | 30 Seconds exposure | 60 Seconds Exposure |
| Ethanol 25% | 0 | 0 |
| Example 1 | 5.8 | 5.8 |
| Example 2 | 5.9 | 6.9 |

Example 42

Virucidal Suspension Test with Human Influenza A Virus

Suspension tests with Human Influenza Virus A were performed using a modification of the Standard Test Method for efficacy of Virucidal Agents (ASTM E1052). Viral strain was Human Influenza Virus A H1N1/A/WS/33 ATCC VR-1520 grown on Madin Darby Canis Kidney cells ATCC CCL-34 (MDCK). A 1.8 ml aliquot of each test substance was dispensed into separate sterile tubes and each was mixed with a 0.2 ml aliquot of the stock virus suspension. The mixtures were mixed for 10 seconds and held the remainder of the exposure time. Immediately following the exposure period, a 0.2 ml aliquot was removed from each tube and the mixtures were tittered by 10-fold serial dilutions and assayed for the presence of virus by infecting indicator cell lines. Cytopathic effect (CPE) was used in each case to indicate infection and TCID50 values were calculated by the method of Spearman Karber. Virus controls, neutralization controls, negative control and cytotoxicity controls were also performed.

The antiviral efficacy of formulations of Examples 15 and 16 were tested as described above for Human Influenza Virus and the results are shown in Tables 3 and 4.

TABLE 3

Antiviral efficacy of Example 15 for Human Influenza Virus

| | Exposure time | |
|---|---|---|
| | 15 Seconds exposure | 60 Seconds Exposure |
| $Log_{10}$ reduction | 4.25 | 4.25 |
| Percent reduction | >99.99% | >99.99% |

TABLE 4

Antiviral efficacy of example 16 for Human Influenza Virus

| | Exposure time | |
|---|---|---|
| | 15 Seconds exposure | 60 Seconds Exposure |
| $Log_{10}$ reduction | 4.25 | 4.25 |
| Percent reduction | >99.99% | >99.99% |

Example 43

Virucidal Suspension Test with Rotavirus for Example 15

Suspension test with Rotavirus WA ATCC VR-2018 for Example 15 was performed using the same procedure as described in Example 42 for Influenza virus. Viral strains were grown on African green monkey embryonic kidney cells ATCC CRL-2378.1 (MA-104).

Results are shown in Table 5

TABLE 5

Antiviral efficacy of Example 15 for *Rotavirus*

| | Exposure time | |
|---|---|---|
| | 15 Seconds exposure | 60 Seconds Exposure |
| $Log_{10}$ reduction | 3 | 3.5 |
| Percent reduction | >99.90% | >99.97% |

Example 44

Virucidal Suspension Test with Feline Calcivirus for Examples 15, 38 and 39

Suspension test with feline calicivirus F-9 ATCC VR782 for Example 15, Example 38, and Example 39 were performed using the same procedure as described in example 42 for Influenza virus. Viral strain were grown on felis catus, kidney cells ATCC CCL-94 (CRFK).

TABLE 6

Antiviral efficacy of Examples 15, 38 and 39 for *Feline Calicivirus*.

| | $Log_{10}$ reduction after 60 seconds exposure |
|---|---|
| Example 15 | 3.0 |
| Example 38 | 4.5 |
| Example 39 | 4.5 |

Example 45

Microbiological Examination of Inhibition Efficiency

The compositions of Example 15 and Example 16 were tested for their antimicrobial efficacy.

Method: 20 gram samples were each inoculated with about $10^7$/ml suspension of *Pseudomonas Aeruginosa* (ATCC 9027), *Staphylococcus Aureus* (ATCC 6538) and *Candida Albicans* (ATCC 9027). At each point time, 1 ml of the inoculated sample was transferred into 100 ml peptone water (PW) and was mixed. Immediately after, 5 ml out of 100 ml were filtered through a 0.45 micrometer membrane filter and the membrane was rinsed with additional 100 ml PW. The membranes were placed on Petri dishes using pour plate technique for bacteria and fungi, respectively and incubated for 48 hours.

TABLE 7

Microbiological Examination of Inhibition Efficiency.

| | | | | CFU/Plate | |
|---|---|---|---|---|---|
| | Microorganism | Type of agar plate | Incubation Temperature | Control | Exposure time - 15 Sec |
| Formulation from Example 15 | Pseudomonas Aeruginosa (ATCC 9027) | M-PA | 42.5° C. | $5.7\text{-}6.1 \times 10^6$ | <10 |
| | Staphylococcus Aureus (ATCC 6538) | Baird Parker | 35° C. | $8.8\text{-}9.0 \times 10^6$ | <10 |
| | Candida Albicans (ATCC 10231) | Sabouraud Dextrose | 24° C. | $6.1\text{-}7.7 \times 10^6$ | <10 |
| Formulation from Example 16 | Pseudomonas Aeruginosa (ATCC 9027) | M-PA | 42.5° C. | $5.7\text{-}6.1 \times 10^6$ | <10 |
| | Staphylococcus Aureus (ATCC 6538) | Baird Parker | 35° C. | $8.8\text{-}9.0 \times 10^6$ | <10 |
| | Candida Albicans (ATCC 10231) | Sabouraud Dextrose | 24° C. | $6.1\text{-}7.7 \times 10^6$ | <10 |

Example 46

Concentrated Surface Sanitizer

| | % w/w |
|---|---|
| Sodium Docusate | 2 |
| Geraniol | 2 |
| Menthol | 2 |
| Ethanol | ad 100 |

Method of preparation: Sodium docusate, geraniol, menthol are added to the ethanol by stirring (Heildolph mixer) until they are completely dissolved. The solution is stored in suitable containers.

Before use, the preparation is diluted with water at a ratio of 1 part concentrated surface sanitizer to varying parts of water such as, for example, 1:0.1, 1:0.2, 1:0.25, 1:0.3, 1:0.4, 1:0.5, 1:1, 1:1.5, 1:2, 1:2.5, and up to 1:100 parts water.

Example 47

Sanitizing Wet Wipes

| | % w/w |
|---|---|
| Ethanol | 70 |
| Sodium Docusate | 0.2 |
| Geraniol | 0.15 |
| Menthol | 0.1 |
| Propylene Glycol | 20 |
| Water to | 100 |

Wipes are impregnated with the composition and packed in sachets or other suitable container. Being composed of substances listed in the EAFUS database, these wipes are suitable for sanitizing food contact surfaces.

Example 48

Sanitizing Lips Wipes

| | % w/w |
|---|---|
| Ethanol | 25 |
| Sodium Docusate | 0.05 |
| Geraniol | 0.07 |
| Menthol | 0.1 |
| Propylene Glycol | 10 |
| Glycerin | 7 |
| Cocoa Butter | 1 |
| Sorbitol | 0.2 |
| Water to | 100 |

Wipes are impregnated with the composition for sanitizing lips.

All references, including publications, patent applications, and patents, cited herein are hereby incorporated by reference to the same extent as if each reference were individually and specifically indicated to be incorporated by reference and were set forth in its entirety herein. In addition, the citation or identification of any reference in this application shall not be construed as an admission that such reference qualifies as prior art with respect to the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An antiviral composition comprising from 7 to 85 wt % ethanol, from 0.01 to 2 wt % docusate salt, and from 0.01 to 2 wt % geraniol, and water, wherein the composition has a greater antiviral effect than the additive antiviral effects of ethanol alone, docusate alone in ethanol, and geraniol alone in ethanol, and wherein the composition, when applied to a surface, is capable of substantially reducing the count of a viral microorganism on the surface to which the composition is applied.

2. The composition of claim 1, further comprising 0.01-2 wt % menthol.

3. The composition of claim 1, further comprising a phospholipid, a glycol, or a combination thereof.

4. The composition of claim 1, wherein the surface comprises one or more surfaces of the hands, skin, mouth cavity, lips, mucosae, food contact surfaces, instruments, food, fruit, skin or skin appendages.

5. The composition of claim 1, wherein the composition is mild, non-irritating, quick drying, non-sticky, non-drying, or any combination of the foregoing, with respect to skin surfaces.

6. The composition of claim 1, wherein the viral microorganism is a Vaccinia virus.

7. The composition of claim 1, wherein the viral microorganism is a non enveloped virus.

8. The composition of claim 7, wherein the virus is a norovirus.

9. The composition of claim 7, wherein the virus is a feline calicivirus.

10. The composition of claim 1, which is capable of exhibiting greater than a 2 $\log_{10}$ kill of the microorganism within 60 seconds of application to the surface.

11. The composition of claim 10, which is capable of exhibiting greater than a 3 $\log_{10}$ kill of the microorganism within 60 seconds of application to the surface.

12. The composition of claim 11, which is capable of exhibiting greater than a 4 $\log_{10}$ kill of the microorganism within 60 seconds of application to the surface.

13. The composition of claim 1, wherein the docusate salt is sodium docusate, potassium docusate or calcium docusate.

14. The composition of claim 13, wherein the docusate salt is sodium docusate.

15. The composition of claim 1, further comprising up to 30 wt % of a glycol.

16. The composition of claim 15, wherein the glycol is propylene glycol.

17. The composition of claim 1, further comprising from about 0.1 wt % to about 15 wt % of a phospholipid.

18. The composition of claim 1, comprising 15-60 wt % ethanol, 0-30 wt % propylene glycol, 0.01-1 wt % docusate salt, 0.01-1 wt % geraniol, and water, and further comprising 0.01-1 wt % menthol, a carbomer, and a neutralizer.

19. The composition of claim 3, comprising 15-60 wt % ethanol, 0-30 wt % propylene glycol, 0.01-1 wt % docusate salt, 0.1-15 wt % phospholipid, 0.01-1 wt % geraniol, and water, and further comprising 0.01-1 wt % menthol, 0.1-1 wt % Vitamin E, carbomer, and neutralizer.

20. The composition of claim 1, comprising 10-25 wt % ethanol, 0.05-0.3 wt % sodium docusate, 0.05-0.3 wt % geraniol, and water, and further comprising 0.01-0.3 wt % menthol.

21. The composition of claim 1, comprising 7-25 wt % ethanol, 0.01-0.3 wt % sodium docusate, 0.01-0.3 wt % geraniol, and water, and further comprising 0.01-0.3 wt % menthol, 0-20 wt % propylene glycol, 0.1-20 wt % soy phospholipid.

22. The composition of claim 1, wherein the composition is in the form of a liquid, a foam, a gel, a spray, a lotion, a solution, an emulsion, or a cream.

23. A method for sanitizing a surface, the method comprising applying the composition of claim 1 to the surface in an amount effective to at least substantially reduce the count of a microorganism, which is a virus, a bacterium, a fungus, a yeast, a mould, or a combination thereof, on the surface.

24. An article of manufacture, comprising a container containing the composition of claim 1 and instructions for applying the composition to a surface so as to sanitize or disinfect the surface.

25. The article of manufacture of claim 24, wherein the instructions comprise instructions to spray, rub or massage the composition onto the skin one or more times daily, as needed.

26. A woven or non-woven wipe, sponge, tissue, roll-on lipstick, or liquid lipstick, comprising the composition of claim 1.

* * * * *